United States Patent [19]

Chikaoka et al.

[11] 4,003,801

[45] Jan. 18, 1977

[54] TREATMENT OF WATER VAPOR GENERATED IN CONCENTRATING AN AQUEOUS UREA SOLUTION

[75] Inventors: Sadashi Chikaoka; Toyotaro Kawabe; Hisashi Miyakawa; Naotoshi Seki, all of Takaishi, Japan

[73] Assignee: Mitsui Toatsu Chemicals, Incorporated, Tokyo, Japan

[22] Filed: May 14, 1975

[21] Appl. No.: 577,341

[30] Foreign Application Priority Data

May 14, 1974 Japan ............................ 49-52891

[52] U.S. Cl. ................................. 203/42; 203/87; 260/555 A
[51] Int. Cl.² ...................................... C07C 126/02
[58] Field of Search ............... 203/39, 42, 48, 87, 203/91; 260/555 A, 555 C; 423/237, 238, 220, 234; 55/70

[56] References Cited

UNITED STATES PATENTS

| | | | |
|---|---|---|---|
| 3,506,710 | 4/1970 | Inoue | 203/42 |
| 3,573,173 | 3/1971 | Otsuka | 203/42 |
| 3,725,210 | 4/1973 | Otsuka | 203/42 |
| 3,944,605 | 3/1976 | Inoue | 260/555 A |

FOREIGN PATENTS OR APPLICATIONS

| | | | |
|---|---|---|---|
| 251,571 | 10/1970 | U.S.S.R. | 260/555 A |

*Primary Examiner*—Hiram H. Bernstein
*Attorney, Agent, or Firm*—Fisher, Christen & Sabol

[57] ABSTRACT

Water vapor generated in concentrating an aqueous urea solution and containing a small amount of aqueous urea solution mist, ammonia and carbon dioxide is treated to recover urea and ammonia values. The water vapor is introduced into a separator wherein all of the urea solution mist is separated together with a part of the ammonia and the carbon dioxide to form a first condensate. The water vapor is then fed into a surface cooler wherein the water vapor is indirectly cooled to form a second condensate. The first condensate is used for process water and the second condensate is subjected to rectification to separate ammonia and carbon dioxide contained therein in the form of a mixed gas, which is recovered, from the remaining waste water free of ammonia and carbon dioxide.

17 Claims, 1 Drawing Figure

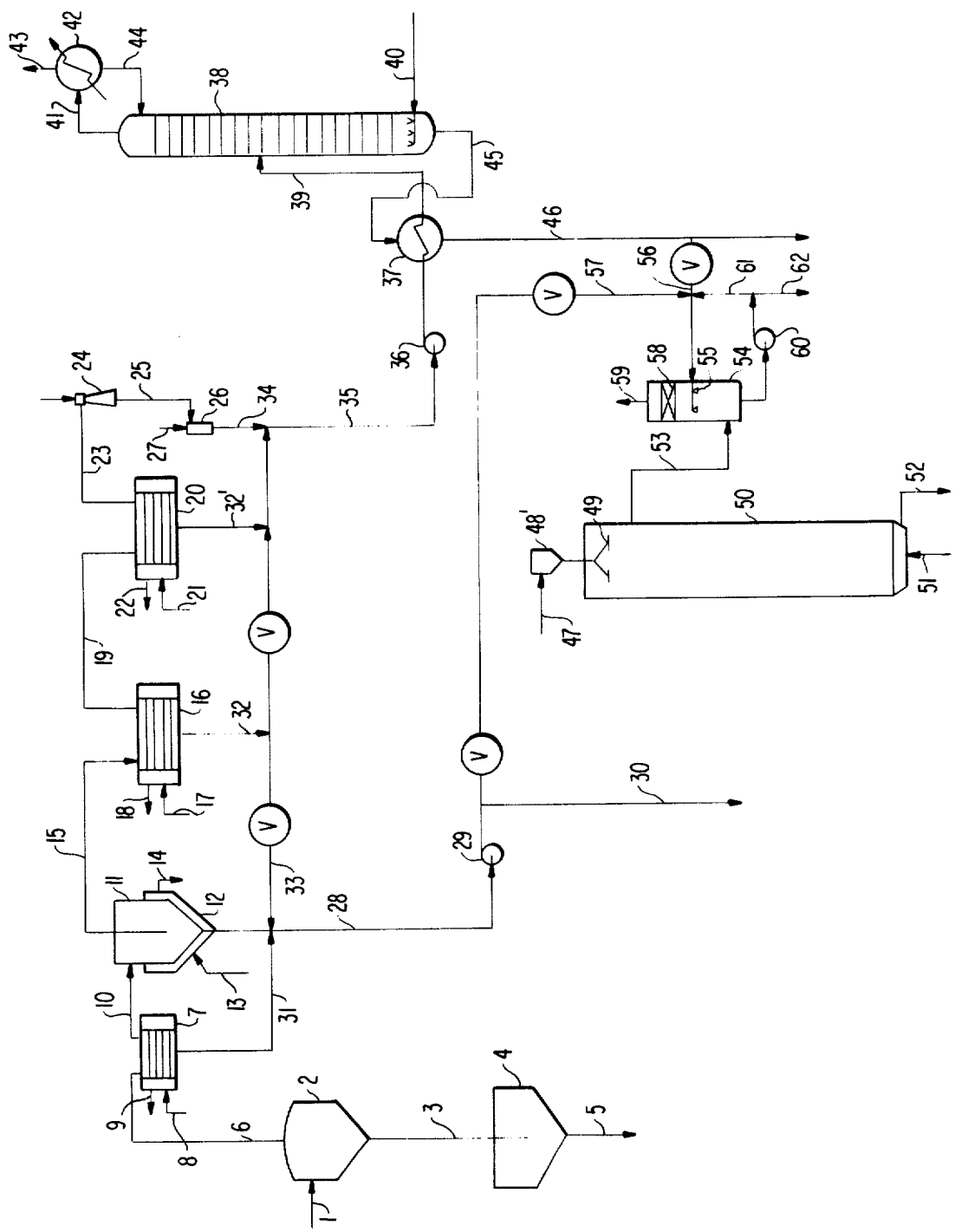

TREATMENT OF WATER VAPOR GENERATED IN CONCENTRATING AN AQUEOUS UREA SOLUTION

BACKGROUND OF THE INVENTION

1. Field of the Invention

This invention relates to a process for treatment of water vapor which is generated in a step of concentrating an aqueous urea solution containing small amounts of ammonia and carbon dioxide.

2. Description of the Prior Art

The production of crystalline urea from carbon dioxide and ammonia has been heretofore carried out by a process wherein the carbon dioxide and ammonia are reacted with each other under urea-systhesis temperatures and pressures to obtain a reaction mixture containing urea, unreacted ammonium carbamate and water, and the reaction mixture is then passed through a plurality of unreacted ammonium carbamate-decomposition stages, the pressures of which are stepwise reduced. Such multi-stage decomposition is generally effected by a two-stage high and low pressure decomposition process, a three-stage decomposition process involving two high pressure stages and one low pressure stage, or an one- or two-stage high pressure and/or low pressure decomposition process which is carried out subsequent to stripping with ammonia or carbon dioxide under a pressure substantially equal to the urea-synthesis pressure, and a separation step involving flashing under normal or reduced pressure is generally provided subsequent to a low pressure decomposition to separate the unreacted ammonium carbamate from the reaction mixture in the form of a mixed gas of ammonia and carbon dioxide. Then the resulting urea solution which contains small amounts of ammonia and carbon dioxide is subjected to concentration, preferably under reduced pressure, to obtain crystalline urea. In the process, water vapor which is generated in the concentration step contains a small amount of a mist of the aqueous urea solution, together with ammonia and carbon dioxide. Accordingly, discharging the condensate formed by condensing this water vapor as it is results not only in water pollution but also in loss of urea and ammonia. In order to avoid these disadvantages, the water vapor has heretofore been condensed by indirect cooling to form a condensate containing urea, ammonia and carbon dioxide, the thus formed condensate is subjected to rectification for separating therefrom a mixed gas of ammonia, carbon dioxide and water vapor, and the mixed gas is recovered to feed back into the urea synthesis step. However, since the waste water discharged from the rectification step still contains some urea, even though a part of the urea is hydrolyzed during the rectification into ammonia and carbon dioxide which are collected together with the above-mentioned mixed gas, discharging this waste water from the urea plant still presents problems of water pollution as well as of loss of urea.

SUMMARY OF THE INVENTION

It is a primary object of the present invention to provide a process for treatment of water vapor generated in a step of concentrating an aqueous urea solution without causing any water pollution or loss of urea.

It has been found that the above object can be attained by an improvement in a process for treatment of water vapor generated in concentrating an aqueous urea solution wherein carbon dioxide and ammonia are reacted at urea synthesis temperatures and pressures, the resulting reaction mixture is passed through a plurality of unreacted ammonium carbamate-decomposition stages, the pressures of which are stepwise reduced, to decompose and separate the unreacted ammonium carbamate from the aqueous urea solution, the aqueous urea solution containing small amounts of ammonia and carbon dioxide is subjected to concentration thereby separating therefrom water vapor containing a mist of the aqueous urea solution, the ammonia and the carbon dioxide, and the water vapor is treated for recovering urea and ammonia values. The improvement of the present invention comprises:

1. separating from the water vapor the aqueous urea solution mist together with a part of the ammonia, carbon dioxide and water vapor to form a first condensate containing urea, ammonia and carbon dioxide,
2. condensing by indirectly cooling the water vapor discharged from step (1) and containing the remaining part of the ammonia and carbon dioxide to from a second condensate containing ammonia and carbon dioxide,
3. subjecting the second condensate to rectification to separate a mixed gas of ammonia and carbon dioxide containing a small amount of moisture from the remaining water which is substantially free of ammonia and carbon dioxide,
4. recovering the mixed gas from step (3), and
5. optionally employing the first condensate as process water.

BRIEF DESCRIPTION OF THE DRAWING

The sole FIGURE is a flow diagram illustrating one preferred embodiment of the invention.

DESCRIPTION OF THE PREFERRED EMBODIMENTS

The present invention will be illustrated in detail by the following detailed description and with specific reference to the drawing.

The aqueous urea solution which is introduced into the concentration step, preferably conducted under reduced pressure, can be produced by reacting ammonia and carbon dioxide in accordance with any of the known processes. Such process are described in, for example, U.S. Pat. Nos. 2,116,881, 3,200,148, 3,317,601, 3,347,915, 3,357,901, 3,390,058, 3,470,247, 3,573,173, and 3,725,210, and the above disclosures are incorporated herein by reference. The resulting urea solution generally contains 60–80% by weight of urea, 0.1–1.0% by weight of ammonia and 0.1–1.0% by weight of carbon dioxide. The urea solution is subjected to concentration, preferably at a temperature of 50°–85° C. under a pressure of 60–200 mmHg to crystallize out crystalline urea. The water vapor from the concentration step contains a mist of the aqueous urea solution, and ammonia and carbon dioxide both contained in the urea solution. The urea, ammonia and carbon dioxide are generally contained in the water vapor in amounts of 0.1–1.2% by weight, 0.3–1.6% by weight and 0.2–1.0% by weight, respectively.

The water vapor from the concentration step is introduced into a separation step for separating the mist of the aqueous urea solution from the water vapor. In the separation step, the water vapor is cooled to and maintained preferably at 40°–90° C. so that a part of the water vapor is condensed together with a part of the ammonia and carbon dioxide contained in the water vapor to form a first condensate. Alternatively, the water vapor may be indirectly cooled prior to the introduction thereof into the separation step to condense a part of the water vapor together with a part of the mist of the aqueous urea solution, ammonia and carbon dioxide to form a precondensate, followed by introduction of the remaining water vapor into the separation step. The resulting first condensate generally contains 1–20% by weight of urea, 0.02–0.1% by weight of ammonia and 0.01–0.1% by weight of carbon dioxide. This first condensate is preferably used as a process water, e.g., in a step for the production of urea such as an absorbent in the recovery step for unreacted ammonium carbamate, a solution for washing crystalline urea in a centrifugal separation step or an absorbent for urea dust contained in cooling air exhausted from a prilling tower.

Then, the water vapor which is discharged from the above-mentioned separation step is condensed by indirect cooling in a condensation step. The condensation is preferably carried out in a plurality of condensing stages. The resulting condensate, referred to herein as the second condensate, generally contains 0–0.05% by weight of urea, 0.3–2.0% by weight of ammonia and 0.2–1.5% by weight of carbon dioxide. This second condensate may be introduced into the rectification step or, if desired, a part of the second condensate may be used as an absorbent in the recovery step for unreacted ammonium carbamate in combination with the first condensate obtained in the separation step, or the second condensate may be employed for washing crystalline urea in the centrifugal separation step. In the rectification step, substantially all of the ammonia and carbon dioxide are separated from the second condensate in the form of a mixed gas which is substantially composed of ammonia and carbon dioxide and which contains a small amount of moisture. Then the depleted second condensate is subjected to heat exchange with fresh second condensate which is being fed into the rectification step, and is then discharged. The mixed gas may be recovered by absorption in an absorbent in the unreacted ammonia carbamate-recovery step or may be recovered by absorption in an acid. On the other hand, the depleted second condensate may be discharged as waste water as it is or may be used as feed water for a boiler by passing the same through an ion exchanger, if necessary, since the depleted second condensate is distilled water produced as the result of evaporation of the aqueous urea solution.

In the rectification step, it is preferable to pass the ammonia and carbon dioxide gases which are fed from the top of the rectification column into a saturated ammonium carbamate aqueous solution at 70°–125° C. to separate substantially all of the moisture therefrom and to obtain a mixed gas containing a small amount of moisture and to feed a part of the aqueous ammonium carbamate solution back into the rectification column at the top thereof.

The process of this invention for treating water vapor generated in the concentration step may be effected in combination with a process for recovery of urea dust from a waste gas which is exhausted from a urea-granulating apparatus or a urea-prilling tower. That is, exit air which is used for cooling molten urea in the prilling tower and which contains urea dust can be washed with the second condensate obtained in the condensation step or/and with the first condensate obtained in the separation step for separating the mist of the aqueous urea solution, or with the waste water discharged from the rectification step to dissolve the urea dust in the condensate. The resulting urea solution may be fed into the vacuum concentration step or otherwise used as process water as described hereinabove.

Referring now particularly to the drawing, an aqueous urea solution which contains 60–80% by weight of urea, 0.1–1.0% by weight of ammonia and 0.1–1.0% by weight of carbon dioxide is fed through line 1 into vacuum concentrator 2 which is kept at a reduced pressure of 60–200 mmHg by means of ejector 24 operated by high pressure steam. The concentration is carried out at a temperature of 55°–70° C. Concentrator 2 is connected through barometric leg 3 with crystallizer 4 in which a slurry of urea is produced. A part of the urea slurry may be either withdrawn through line 5 for centrifugal separation or fed as it is to a second concentration step, not shown, to obtain molten urea which is substantially free from moisture. The separated crystals of urea may be washed and dried to give a final product or fed to a prilling step. Furthermore, some of the urea slurry may be withdrawn and passed through a heating device, not shown, and the thus heated slurry may be fed to vacuum concentrator 2 for use as a heating source for concentration.

The water vapor from vacuum concentrator 2 containing 0.1–1.2% by weight of urea in the form of an aqueous urea solution mist, 0.3–1.6% by weight of ammonia and 0.2–1.0% by weight of carbon dioxide is fed through line 6 into pre-cooler 7 in which a part of the aqueous area solution mist is condensed together with a part of the water vapor, ammonia and carbon dioxide to form a precondensate by cooling with water introduced through line 8 and discharged through line 9. Pre-cooler 7 may be omitted in some cases. The water vapor stream discharged from pre-cooler 7 is introduced through line 10 into separator 11 for separating therefrom the aqueous urea solution mist. Though separators of various types can be used as separator 11, a cyclone separator with a cooling jacket 12, is, for example, useful for this purpose. The temperature of separator 11 is maintained at 40°–60° C. by means of cooling water which is introduced into cooling jacket 12 through line 13 and discharged through line 14, so that substantially all of the aqueous urea solution mist, 1–10% by weight of the ammonia and 0.5–5% by weight of the carbon dioxide, which are contained in water vapor fed into separator 11, are condensed together with a part of the water vapor to form a first condensate. In this connection, the condensate-separation in separator 11 may be facilitated by introducing into separator 11 an absorbent for ammonia and carbon dioxide such as condensates which are obtained in separator 11, first condenser 16, second condenser 20 and barometric condenser 26, as will be described hereinafter.

The water vapor discharged from separator 11 is fed through line 15 into first condenser 16 in which the same is indirectly cooled with water introduced through line 17 and discharged through line 18 thereby condensing some of the water vapor to form a portion of a second condensate which is a dilute aqueous ammonium carbamate solution. The water vapor discharged from first condenser 16 is then fed through line 19 into second condenser 20 and is indirectly cooled with water which is introduced through line 21 and discharged from line 22. As a result, most of the water vapor is condensed to form another portion of a second condensate which is a dilute aqueous ammonium carbamate solution. The water vapor which is not yet condensed in second condenser 20 is passed through line 23 into ejector 24 operated by high pressure steam and is fed together with the high pressure steam through line 25 into barometric condenser 26 in which the steam is condensed by directly cooling with water introduced through line 27 to form a third condensate which is a dilute aqueous ammonium carbamate solution. To barometric condenser 26 may be fed a part of the second condensate from line 35 or the third condensate from 34 instead of the cooling water. It should be noted that condensation of the water vapor discharged from separator 11 is not limited to the above-described two-stage process, but may be effected by an arbitrary number-stage condensation process including one-stage or three- or greater stage condensations.

The first condensate obtained in separator 11 is fed through line 28, pump 29 and line 30 for use as process water together with the precondensate which is withdrawn from the pre-cooler 7 through line 31. Part or all of the portion of the second condensate which is taken out from first condenser 16 through lines 32 and 33 may also be used as process water. The process water is employed, for example, to wash urea crystals obtained in a centrifugal separator, as an absorbent to be used in the recovery of unreacted ammonium carbamate, or as an absorbent for urea dust contained in the cooling air exhausted from a prilling tower. Prior to employment of these condensates as process water, part or all of the condensates may be subjected to rectification for separating a mixed gas of ammonia and carbon dioxide. Furthermore, a part of the condensates may be passed into vacuum concentrator 2 instead of being used as process water.

The condensates which are produced in first condenser 16 and second condenser 20 (second condensate) and in barometric condenser 26 (third condensate) are gathered together through lines 32, 32' and 34, respectively, and fed through line 35 and pump 36 into heat exchanger 37 for heat exchange with hot water discharged from the bottom of rectification column 38 and then fed through line 39 into the middle part of rectification column 38 which is operated under a pressure of 0.5–3.0 kg/cm² (gauge). Steam for heating is fed into the bottom of rectification column 38 through line 40. A mixed gas of ammonia, carbon dioxide and water vapor which is discharged from the top of rectification column 38 is passed through line 41 into condenser 42 wherein the same is brought into contact with a condensate of the mixed gas (an aqueous ammonium carbamate solution) at 70°–125° C. for removing therefrom part of the water vapor, and is then discharged from line 43. The resulting mixed gas which contains 10–60% by weight of ammonia, 5–40% by weight of carbon dioxide and 6–80% by weight of water vapor is fed for absorption into an unreacted ammonium carbamate recovering step, not shown. The mixed gas may be recovered by absorption in sulfuric acid, phosphoric acid or the like. The condensate obtained in condenser 42 is circulated through line 44 to the top of rectification column 38. From the bottom of rectification column 38 hot water containing ammonia in an amount of less than 0.05% by weight is discharged and fed through line 45 into heat exchanger 37 in which, as described hereinabove, the same is subjected to heat exchange with the condensate which is being introduced into rectification column 38. The thus cooled water may be either discharged as waste through line 46 or used for some other purpose. Particularly, the cooled water is preferably used as feed water for a boiler by passing it through an ion exchanger, not shown, since the load of the ion exchanger will decrease (i.e., the water is originally distilled water and contains no substances other than small amounts of ammonia and carbon dioxide). Alternatively, the cooled water may be used for washing cooling air discharged from a prilling tower to remove therefrom urea dust, as will be described hereinafter.

The process of the invention is feasible even in combination with the removal of urea dust from cooling air exhausted from a prilling tower. To illustrate this in detail, molten urea is introduced through line 47 into tank 48, from which the molten urea is dropped in the form of droplets through a nozzle plate 49 into prilling tower 50. The droplets are cooled and solidified during dropping by contact with cooling air which is fed into the bottom of prilling tower 50 through line 51 and the resulting granular urea is taken out from the bottom of prilling tower 50 through line 52. The cooling air discharged from the top of prilling tower 50 generally contains 100–1,000 mg/m³ of urea dust. The discharged air is passed through line 53 into washing tower 54 wherein it is sprayed through nozzles 55 with water which is introduced from line 56 and/or the first condensate, which is fed by means of pump 29 through line 27, for washing and removing the major part of the urea dust therefrom. Then, the remaining dust is collected within tower 54 by filtering through layers 58 of a foamed resin having an open cellular porosity of greater than 90%. The air separated from the urea dust is exhausted through line 59. On the other hand, the solution discharged from washing tower 54 generally contains 10–30% by weight of urea, part of the solution being circulated by means of pump 60 to washing tower 54 through line 61 and the remainder being withdrawn through line 62 for use as process water or for treatment after feeding it to vacuum concentrator 2.

In accordance with the present invention, there can be recovered substantially all of the urea, ammonia and carbon dioxide which are contained in the water vapor generated in concentrating an aqueous urea solution to avoid water pollution by waste water. Furthermore, where ammonia and carbon dioxide are separated by rectification from the second condensate the resulting waste water contains no urea since there is no urea present in the second condensate fed into the rectification column. Accordingly, in the rectification step, no loss of urea by hydrolysis thereof into ammonia and carbon dioxide can occur. In addition, the process of the invention needs only a slight increase of steam consumption over that conventionally used.

The present invention will be particularly illustrated by way of the following example, which is illustrative only and should not be construed as limiting the present invention.

EXAMPLE

800 Tons per day of water vapor which was generated from vacuum concentrator 2 operated at 55° C. under a pressure of 72 mmHg and which contained 2.7 tons per day of urea (in the form of a mist of an aqueous urea solution), 4.2 tons per day of ammonia and 2.1 tons per day of carbon dioxide was fed into pre-cooler 7 and then into cyclone-type separator 11 provided with cooling jacket 12 in which the water vapor was cooled to 45° C. to separate all of the urea and a part of the ammonia and carbon dioxide by condensation from the water vapor. The resulting condensate (which was a combination of the precondensate obtained in pre-cooler 7 and the first condensate obtained in separator 11) contained 2.7 tons per day of urea, 0.05 tons per day of ammonia, 0.02 tons per day of carbon dioxide and 18.6 tons per day of water.

The water vapor discharged from separator 11 was passed through first and second condensers 16 and 20, respectively, for further condensation to form a second condensate. The water vapor which was discharged from second condenser 20 was then fed into ejector 24 together with high pressure steam which was passed through the ejector for operating the same thereby to form a third condensate which contained 4.15 tons per day of ammonia, 2.08 tons per day of carbon dioxide and 830 tons per day of water. A part of the third condensate was circulated to barometric condenser 26 after cooling.

The first condensate formed in separator 11 was fed to a centrifugal separation step for urea crystals to wash the crystals. The second and third condensates which were formed in first and second condensers 16 and 20, and in barometric condenser 26, respectively, were combined and pressurized to a gauge pressure of 2.5 kg/cm² and passed through heat exchanger 37 wherein the combined condensate was heated to 120° C. by heat exchange with hot water of 143° C. discharged from rectification column 38. The thus heated combined condensate was fed to rectification column 38 at the middle part thereof. A mixed gas at 105° C. which was exhausted from the top of rectification column 38 and which contained 4.58 tons per day of ammonia, 2.64 tons per day of carbon dioxide and 3.78 tons per day of water vapor was introduced into condenser 42 in which the same was contacted with a condensate of the mixed gas (an aqueous ammonium carbamate solution) maintained at 90° C. and was discharged in the form of a mixed gas composed of 4.07 tons per day of ammonia, 2.08 tons per day of carbon dioxide and 1.79 tons per day of water vapor. The mixed gas was fed for absorption into a low pressure absorption column in the unreacted ammonium carbamate recovery system. From condenser 42 0.51 tons per day of ammonia, 0.56 tons per day of carbon dioxide and 2.0 tons per day of water were fed to the top of rectification column 38. On the other hand, 0.08 tons per day of ammonia and 827.6 tons per day of water at 143° C. were discharged from the bottom of rectification column 38. The thus discharged solution was subjected to heat exchange with the combined condensate which was being fed into rectification column 38 to cool the same to 69° C. as described hereinbefore. A part of the combined condensate was used for washing urea dust from the cooling air of prilling tower 50, and the remaining part was further cooled by contact with an air stream for use as cooling water. In the process of this example, only a slight additional amount of steam in the amount of 0.003 tons per ton of urea was required over that required in the conventional process.

What is claimed is:

1. In the process for treatment of water vapor generated in concentrating an aqueous urea solution obtained by reacting carbon dioxide and ammonia at urea synthesis temperatures and pressures, wherein the resulting reaction mixture is passed through a plurality of unreacted ammonium carbamate decomposition stages, the pressures of which are stepwise reduced, to decompose and separate the unreacted ammonium carbamate from the aqueous urea solution, the aqueous urea solution containing small amounts of ammonia and carbon dioxide is subjected to concentration to separate therefrom water vapor containing a mist of the aqueous urea solution, ammonia and carbon dioxide, and the water vapor is treated to recover urea and ammonia values, the improvement which comprises:
    1. separating from the water vapor the mist of the aqueous urea solution together with a part of the ammonia, carbon dioxide and water vapor to form a first condensate containing urea, ammonia and carbon dioxide,
    2. condensing by indirect cooling the water vapor discharged from step (1) and containing the remaining part of the ammonia and carbon dioxide to form a second condensate containing ammonia and carbon dioxide,
    3. subjecting the second condensate to rectification in a rectification zone to separate a mixed gas of ammonia and carbon dioxide containing a small amount of moisture, from water substantially free of ammonia and carbon dioxide, and
    4. recovering the mixed gas from step (3).

2. The process as claimed in claim 1 wherein the concentration is conducted at a pressure of 60 to 200 mmHg.

3. The process as claimed in claim 1 wherein the separation of step (1) is conducted under indirect cooling.

4. The process as claimed in claim 3 wherein an absorbent for ammonia and carbon dioxide is fed into the separation of step (1).

5. The process as claimed in claim 1 wherein the water vapor is cooled indirectly prior to feeding into the separation of step (1) thereby condensing a part of the aqueous urea solution mist together with a part of the water vapor, ammonia and carbon dioxide to form a precondensate.

6. The process as claimed in claim 1 wherein the condensation of step (2) is conducted in two stages.

7. The process as claimed in claim 1 wherein the water vapor discharged from step (2) is condensed by mixing with water or a dilute aqueous ammonium carbamate solution to form a third condensate.

8. The process as claimed in claim 7 wherein the third condensate is subjected to rectification together with the second condensate.

9. The process as claimed in claim 1 wherein the mixed gas from step (3) is passed through a saturated ammonium carbamate solution having a temperature of 70° to 125° C., thereby condensing a part of the moisture contained therein, and a part of the saturated ammonium carbamate solution is fed back into the top of the rectification zone.

10. The process as claimed in claim 1 wherein the second condensate is subjected to heat exchange with hot waste water discharged from the rectification zone prior to subjecting said second condensate to rectification.

11. The process as claimed in claim 1 wherein the first condensate is used as process water in urea production.

12. The process as claimed in claim 11 wherein the first condensate is combined with the precondensate.

13. The process as claimed in claim 1 wherein the first condensate is used for washing urea dust from the cooling air stream exhausted from a urea prilling zone.

14. The process as claimed in claim 13 wherein the air stream discharged after washing of urea dust therefrom is filtered through a layer of a foamed resin having an open cellular porosity of over 90 percent to remove substantially all of the remaining urea dust therefrom.

15. The process as claimed in claim 13 wherein the first condensate is combined with the waste water discharged from the rectification zone.

16. The process as claimed in claim 13 wherein a part of the first condensate having urea dust absorbed therein is circulated for further washing of urea dust from the cooling air stream.

17. The process as claimed in claim 13 wherein the first condensate having urea dust absorbed therein is fed into the concentration of the aqueous urea solution.

* * * * *